United States Patent
Palmer et al.

(10) Patent No.: US 11,760,056 B2
(45) Date of Patent: Sep. 19, 2023

(54) FLEXIBLE FOAM RESISTIVE HEATERS AND METHODS OF MAKING FLEXIBLE RESISTIVE HEATERS

(71) Applicant: Battelle Memorial Institute, Columbus, OH (US)

(72) Inventors: Katherine Palmer, Columbus, OH (US); Amy M. Heintz, Dublin, OH (US); Brett R. Burton, Powell, OH (US); Scott Danhof, Plain City, OH (US); Jeff Ellis, Columbus, OH (US)

(73) Assignee: Battelle Memorial Institute, Columbus, OH (US)

( * ) Notice: Subject to any disclaimer, the term of this patent is extended or adjusted under 35 U.S.C. 154(b) by 565 days.

(21) Appl. No.: 16/705,173

(22) Filed: Dec. 5, 2019

(65) Prior Publication Data

US 2020/0189229 A1 Jun. 18, 2020

Related U.S. Application Data

(60) Provisional application No. 62/775,824, filed on Dec. 5, 2018.

(51) Int. Cl.
| | | |
|---|---|---|
| *B32B 5/18* | (2006.01) | |
| *A61M 15/00* | (2006.01) | |
| *C08K 3/04* | (2006.01) | |
| *B32B 5/22* | (2006.01) | |

(52) U.S. Cl.
CPC ............ *B32B 5/18* (2013.01); *A61M 15/0001* (2014.02); *B32B 5/22* (2013.01); *C08K 3/042* (2017.05); *B32B 2255/26* (2013.01); *B32B 2305/022* (2013.01); *B32B 2307/306* (2013.01)

(58) Field of Classification Search
CPC . B32B 5/22; B32B 2255/26; B32B 2305/022; B32B 2307/306; A61M 15/0001; C08K 3/042; H05B 3/34; H05B 2203/013; H05B 2203/017; H05B 2214/04; H05B 3/145

See application file for complete search history.

(56) References Cited

U.S. PATENT DOCUMENTS

| | | | |
|---|---|---|---|
| 4,922,901 | A | 5/1990 | Brooks et al. |
| 4,931,479 | A | 6/1990 | Morgan |
| 6,729,269 | B2 | 5/2004 | Ott et al. |

(Continued)

FOREIGN PATENT DOCUMENTS

| | | | |
|---|---|---|---|
| CN | 102557022 | * | 7/2012 |
| DE | 102007001132 A1 | | 7/2008 |

(Continued)

OTHER PUBLICATIONS

Machine translation of Description of German Patent DE 102007001132 A1.

(Continued)

*Primary Examiner* — Kevin R Kruer
(74) *Attorney, Agent, or Firm* — Frank Rosenberg; Susanne A. Wilson

(57) ABSTRACT

Flexible foam resistive heaters prepared with conductive coatings are described. The invention also includes methods of making flexible lead (busbar) connections with low contact resistance for superior uniformity and lower power utilization than conventional technology.

19 Claims, 6 Drawing Sheets

(56) References Cited

U.S. PATENT DOCUMENTS

| | | | |
|---|---|---|---|
| 6,924,467 B2 | 8/2005 | Ellis et al. | |
| 7,473,411 B2* | 1/2009 | Ajayan | H01M 4/583 |
| | | | 428/605 |
| 7,786,408 B2 | 8/2010 | Augustine et al. | |
| 9,263,170 B2 | 2/2016 | Foss | |
| 9,380,813 B2 | 7/2016 | McCullough | |
| 9,538,855 B2 | 1/2017 | Gross et al. | |
| 9,894,715 B2 | 2/2018 | Zirgel | |
| 9,919,274 B2* | 3/2018 | Mitra | B01D 71/40 |
| 10,002,686 B2 | 6/2018 | Sotzing et al. | |
| 10,172,387 B2 | 1/2019 | Davis et al. | |
| 10,183,754 B1 | 1/2019 | Agarwal et al. | |
| 10,193,209 B2 | 1/2019 | Blair | |
| 10,456,754 B2* | 10/2019 | Hogen-Esch | B01D 67/0006 |
| 10,501,845 B2* | 12/2019 | Farquhar | C23C 16/045 |
| 2006/0052020 A1 | 3/2006 | Marmarpoulos | |
| 2010/0051604 A1 | 3/2010 | Davidov | |
| 2012/0022620 A1 | 1/2012 | Khodak et al. | |
| 2012/0026643 A1* | 2/2012 | Yu | H01G 11/46 |
| | | | 977/932 |
| 2012/0028798 A1* | 2/2012 | Worsley | C01B 33/027 |
| | | | 252/502 |
| 2013/0078447 A1* | 3/2013 | Kow | C08J 5/04 |
| | | | 156/60 |
| 2013/0277359 A1 | 10/2013 | Fukuda | |
| 2015/0147525 A1* | 5/2015 | Maruyama | C23C 16/0263 |
| | | | 204/192.12 |
| 2016/0002043 A1* | 1/2016 | Zhang | C01B 32/174 |
| | | | 252/502 |
| 2016/0013390 A1* | 1/2016 | Nishio | H01L 35/32 |
| | | | 136/205 |
| 2016/0332121 A1* | 11/2016 | Datta | B01D 67/0046 |
| 2017/0029279 A1* | 2/2017 | Kim | C01B 32/186 |
| 2019/0360958 A1* | 11/2019 | Choa | G01N 33/005 |
| 2020/0009846 A1* | 1/2020 | Lin | B32B 25/14 |
| 2020/0189229 A1* | 6/2020 | Palmer | H05B 3/145 |
| 2020/0227734 A1* | 7/2020 | Zhamu | H01M 4/386 |
| 2020/0238576 A1* | 7/2020 | Christy | B29C 35/02 |
| 2020/0313135 A1* | 10/2020 | Stainer | H01M 50/46 |
| 2020/0381708 A1* | 12/2020 | Stowell | C01B 32/21 |
| 2020/0399131 A1* | 12/2020 | Thekkekara | C01B 32/192 |
| 2021/0197140 A1* | 7/2021 | Flint | B01D 67/0046 |
| 2021/0207815 A1* | 7/2021 | Schrödner | H05B 1/0202 |
| 2021/0313634 A1* | 10/2021 | Zhamu | H01M 50/284 |
| 2022/0166029 A1* | 5/2022 | Zhamu | H01M 4/662 |
| 2022/0169158 A1* | 6/2022 | Cauchy | F25B 21/04 |

FOREIGN PATENT DOCUMENTS

| | | |
|---|---|---|
| EP | 3442309 A1 | 2/2019 |
| GB | 2238722 A | 6/1991 |
| WO | 2010143153 A1 | 12/2010 |
| WO | 2018146592 A1 | 8/2018 |
| WO | 2018157208 * | 9/2018 |

OTHER PUBLICATIONS

International Preliminary Report on Patentability in International Application No. PCT/US2019/064791, dated Jun. 8, 2021.
International Search Report and Written Opinion in International Application No. PCT/US2019/064791, dated Feb. 13, 2020.
Machine Translation, EP Application No. 3442309, published Feb. 13, 2019.
First Office Action in European Application No. EP19828134.7A dated Sep. 12, 2022.

* cited by examiner

FLEXIBLE FOAM RESISTIVE HEATERS AND METHODS OF MAKING FLEXIBLE RESISTIVE HEATERS

RELATED APPLICATIONS

This application claims the priority benefit of U.S. Provisional Patent Application Ser. No. 62/775,824, filed 5 Dec. 2018.

INTRODUCTION

Flexible resistive heaters are commonly used in consumer devices such as heating blankets. Generally, these devices incorporate heating wires, coated fabrics or printed circuits laminated between dielectric substrates. These devices can be only slightly flexible (conformal) and, for hospital use are sometimes placed under foam pads to provide suitable pressure management and minimize bed sores. The warming system should not impact the pressure management of a torso pad or headrest. While there are many thin film laminate and/or fabric heaters on the market, their rigidity impacts the pressure management system; and they also have insufficient durability to undergo repeated flexing.

Furthermore, safe warming requires a uniform and consistent temperature, generally in the range of 39° C. Most systems place the heater under the foam pressure management system. This has several disadvantages. Thermal conduction must occur through an insulating foam. To achieve the target temperature set-point rapidly at the surface, requires high power. In addition, when pressure is applied to the foam, such as when a patient's head is placed on the foam, a hot spot occurs at the contact point. The hot spot occurs because the thickness of the insulation changes, the contact resistance between the foam and the heater changes, and/or the thermal properties of the foam change. Thus, there remains a need for improved flexible and conformal resistive heating devices for warming patients in an operating room.

There are examples in the prior art of flexible bus bar interfaces for heating elements. Augustine et al, in U.S. Pat. No. 7,786,408, describes a copper braid stitched into a folded flexible heating fabric for a patient warming blanket. This patent states that the non-conductive layer comprises a non-woven polymer fabric, woven polymer fabric or cellulose material. This reference does not describe the use of a flexible compressible foam as a non-conductive layer.

SUMMARY OF THE INVENTION

In one aspect, the invention provides a method of making a resistively heatable flexible, foam, comprising: providing a flexible, polymeric solid foam; applying a CNT, graphene, or graphene oxide dispersion to at least one surface of the foam; wherein the CNT, graphene, or graphene oxide dispersion penetrates into the foam; drying the dispersion to form a CNT, graphene, or graphene oxide layer at least partly within the foam; and applying a polymeric film over the CNT, graphene, or graphene oxide layer.

The invention also provides a resistively-heatable flexible, foam, comprising: a flexible, polymeric solid foam; a resistively-heatable CNT, graphene, or graphene oxide layer disposed on the exterior and at least partly within the foam; and a polymeric film disposed over the resistively-heatable CNT, graphene, or graphene oxide layer. In some embodiments, a heat releasable composition is disposed in thermal contact with the resistively-heatable layer. The heat releasable composition can be adsorbed on the polymeric film or impregnated into foam such as in the cells of the foam or within channels or other voids in the foam. The invention also provides a resistively-heatable flexible, foam, comprising: a flexible, polymeric solid foam; a resistively-heatable CNT, graphene, or graphene oxide layer disposed on the exterior and at least partly within the foam; and a heat releasable composition is disposed in thermal contact with the resistively-heatable layer. The resistively heatable layer is preferably in electrical contact with electrodes. The resistively-heatable layer may comprise a dispersant or an adhesive.

In another aspect, the invention provides a method of making a resistively heatable flexible, fabric, comprising: providing a flexible, polymeric solid fabric; applying a CNT, graphene, or graphene oxide dispersion to at least one surface of the fabric; drying the dispersion to form a CNT, graphene, or graphene oxide layer on the surface of the fabric; applying two electrical leads in electrical contact with the CNT, graphene, or graphene oxide layer; and applying a polymeric film over the CNT, graphene, or graphene oxide layer. The electrical leads to the CNT, graphene, or graphene oxide layer can be stitched into or onto the foam wherein the stitches go through the CNT, graphene, or graphene oxide layer and into the foam, and, preferably, the stitches are nonconductive.

In another aspect, the invention provides a resistively-heatable flexible, foam, comprising: a flexible, polymeric solid foam; a resistively-heatable layer disposed on the exterior and at least partly within the foam; at least two electrical leads attached to the foam and electrically connected to the resistively-heatable layer; and further characterizable by one or any combination of the following properties: a surface hardness, measured according to ASTM D2240 on the surface of the heatable flexible foam that is nearest the heatable layer, of 10 to 50 or 20 to 40; the leads having a contact resistance of 50 to 600 ohms, or 50 to 400 or less than 200 ohms when current is applied to the electrodes; the surface having an average surface resistance of 10 to 200 ohms, or 20 to 100 ohms; a power density of 0.1 to 0.5 W/in$^2$ about 0.2 to 0.5 W/in$^2$; or about 0.2 to 0.4 W/in$^2$ or about 0.2 to about 0.3 W/in$^2$ necessary to increase the average temperature of the layer from 75° F. (24 C) to 107° F. (41.7° C.); and/or where the electrical leads are separated by at least three inches or at least 5 inches and having a maximum variation of temperature between the leads and the surface of the heated area of 30° F. (16.7° C.) or less, preferably 25° F. (13.9° C.) or less, more preferably 20° F. (11.1° C.) or less, still more preferably 10° F. (5.5° C.) or less, and in some embodiments in the range of 3 to 10° F. (1.7 to 5.5° C.) when the average temperature of the layer is raised to 107° F. (41.7° C.). For example, in some preferred embodiments, the surface of the heatable flexible foam that is nearest the heatable layer, having a surface hardness of 10 to 50; or wherein the leads have a contact resistance of 50 to 400 ohms when current is applied to the electrodes sufficient to raise the temperature of the layer to 107° F.; or wherein the electrical leads are separated by at least five inches and wherein a maximum variation of temperature between the leads and a surface of the heated area is 20° F. or less when the average temperature of the layer is raised to 107° F.

Generally, any of the inventive aspects can be defined with reference to any of the properties, including ranges of properties, that are shown in the examples. The invention includes articles having ±30% or 20% or 10% of the values shown in the examples. Likewise, any of the inventive aspects can be described in conjunction with the properties described above.

The invention also includes foams and heaters made by the inventive methods. It is believed that articles made by the inventive methods are superior to foams having CNTs uniformly dispersed in a composite material.

The invention also includes a method of warming a patient, comprising: contacting the patient with the resistively-heatable foam described herein; and applying a current through the resistively-heatable CNT, graphene, or graphene oxide layer.

By incorporating the heating element directly onto the foam pad, we can eliminate the need for a separate thermal electric heater and the heating element is located closer to the desired location. The low viscosity of the aqueous conductive coating allows it to filter into the foam and form a 3-dimensional conductive layer on the cell walls of the foam. This 3D structure provides more points of electrical contact to the copper braid bus bar as the foam is compressed and providing an intimate contact needed for good electrical connection to occur. This electrical contact can be further improved by applying additional conductive coating (preferably the CNT, graphene or graphene oxide dispersion) over and through the lead wires.

Throughout the descriptions herein, the phrase "CNT, graphene, or graphene oxide" includes mixtures of these, or in various embodiments, any of the inventive aspects may be defined as comprising one or any combination of these. CNT (carbon nanotubes) is especially preferred. Throughout the descriptions herein, the CNT, graphene, or graphene oxide layer preferably comprises at least 50, 60, 70, 80, 90, or 95 mass % carbon. Preferably, the method includes a step of applying two electrical leads in electrical contact with the CNT, graphene, or graphene oxide layer. The electrical leads can be over (toward the external surface), under or both over and under the restively heatable layer. The electrical leads to the CNT, graphene, or graphene oxide layer can be stitched into or onto the foam wherein the stitches go through the CNT, graphene, or graphene oxide layer and into the foam, and, preferably, the stitches are nonconductive. Typically, conductive material in the CNT, graphene, or graphene oxide layer consists essentially of or is CNT and/or graphene (graphene oxide may be converted to graphene or a graphene-like conductor), and in some preferred embodiments, the conductive component of the CNT, graphene, or graphene oxide layer consists essentially of CNTs.

Preferably, the conductive coating in this invention is comprised of carbon nanotubes. Carbon nanotubes (CNTs) can be formulated into a suspension and deposited on a surface to produce a film of interpenetrating CNTs, called CNT networks. These CNT networks are of interest in applications including transparent electrodes; electrically conductive coatings for EMI shielding or lightning strike protection; and heaters for aircraft anti-icing. CNTs can also be formulated into macroscopic fibers and threads that can be used for applications including electronic textiles, non-metallic wiring, or lightning strike protection. In all these applications, the contact resistance to the bus bars is important for efficient power utilization.

The invention is often characterized by the term "comprising" which means "including," and does not exclude additional components. For example, the phrase "a dispersion comprising CNTs" does not exclude additional components. The invention includes narrower aspects in which the term "comprising" is replaced by the more restrictive terms "consisting essentially of" or "consisting of."

DETAILED DESCRIPTION OF THE INVENTION

Figure 1:
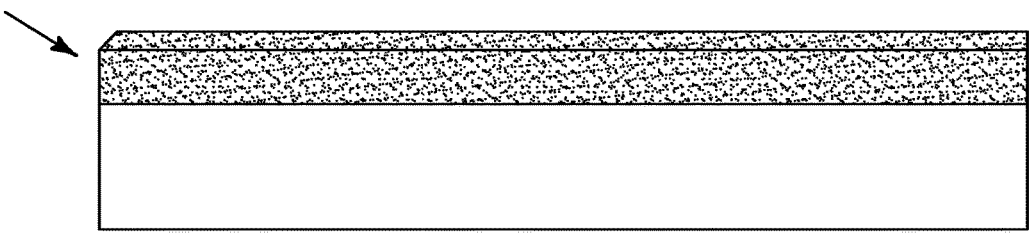
FIG. 1 illustrates a foam having a surface region that is infused with a conductive coating.

In a first aspect, the invention relates to devices that employ a carbon nanotube- or graphene-based conductive coating applied to flexible foam substrates. Suitable foams for these types of novel heaters are either closed, or preferably open cell foams including viscoelastic "memory" foams of any density. The coating is applied to the surface of the foam, and it absorbs into foam coating the walls of the foam cells. The coating remains flexible when dry. The optional addition of a suitable polymeric binder to the conductive coating also ensures adhesion of the conductive coating during handling and compression of the foam.

Viscoelastic foams are well-known for their comfort as mattresses, pillows (also called headrests), and seat cushions. In some preferred embodiments, the foams have one or more of the following properties: a cells/cm of 5 to 50, a density of 20 to 90 kg/m$^3$. In some preferred embodiments, the foam is made with cell opening surfactants (for example, Ortegol 75® ) siloxane oils, polyether siloxanes, and/or silicone foam stabilizers. Some preferred foams are polyurethane. Residual amounts of these processing additives can be left in the foam. Flexible foams are well-known and workers skilled in this area of technology will understand that flexible foams refer to foams that flex when squeezed or compressed and generally do not crumble and recover their shape after (though not necessary immediately after) the compressive force is removed.

A resistive heating layer comprising carbon nanotubes is deposited on the flexible foam. The term "carbon nanotube" or "CNT" includes single, double and multiwall carbon nanotubes and, unless further specified, also includes bundles and other morphologies. The invention is not limited to specific types of CNTs. The CNTs can be any combination of these materials, for example, a CNT composition may include a mixture of single and multiwall CNTs, or it may consist essentially of DWNT (double-walled) and/or MWNT, or it may consist essentially of SWNT (single-walled), etc. CNTs have an aspect ratio (length to diameter) of at least 50, preferably at least 100, and typically more than 1000. In some embodiments, a CNT network layer is continuous over a substrate; in some other embodiments, it is formed of rows of CNT networks separated by rows of polymer (such as CNTs deposited in a grooved polymer substrate). The CNTs may be made by methods known in the art such as arc discharge, CVD, laser ablation, or HiPco.

In some preferred embodiments, a CNT dispersion is made by combining CNTs with glycosaminoglycans. Glycosaminoglycans are long unbranched polysaccharides consisting of a repeating disaccharide unit. The repeating unit (except for keratan) consists of an amino sugar (N-acetylglucosamine or N-acetylgalactosamine) along with a uronic sugar (glucuronic acid or iduronic acid) or galactose. Glycosaminoglycans are highly polar. Anionic glycosaminoglycans are characterized by having at some hydroxyl protons replaced by a counter ion; typically an alkali or alkaline earth element. Examples of glycosaminoglycans include: β-D-glucuronic acid, 2-O-sulfo-β-D-glucuronic acid, α-L-iduronic acid, 2-O-sulfo-α-L-iduronic acid, β-D-galactose, 6-O-sulfo-β-D-galactose, β-D-N-acetylgalactosamine, β-D-N-acetylgalactosamine-4-O-sulfate, β-D-N-acetylgalactosamine-6-O-sulfate, β-D-N-acetylgalactosamine-4-O, 6-O-sulfate, α-D-N-acetylglucosamine, α-D-N-sulfoglucosamine, and α-D-N-sulfoglucosamine-6-O-sulfate. Hyaluronan is a particularly preferred glycosaminoglycan and representative of its class.

A particularly preferred glycosaminoglycan is sodium hyaluronate. Sodium hyaluronate is the sodium salt of hyaluronic acid (HA). Materials such as sodium hyaluronate are natural products. These may be isolated from animal sources or extracted from bacteria. Hyaluron is a viscoelastic, anionic, nonsulfated glycosaminoglycan polymer (shown below). It is found naturally in connective, epithelial, and neural tissues. Its chemical structure

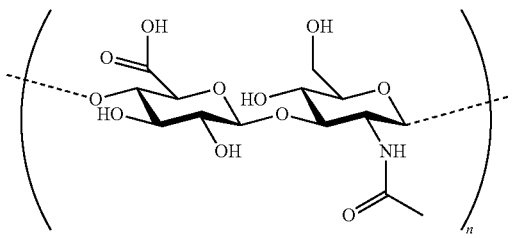

and high molecular weight make it a good dispersing agent and film former. CNT/HA aqueous dispersion and phase diagram has been reported in the literature (Moulton et al. J. Am. Chem. Soc. 2007, 129(30), 9452). These dispersions may be used to create conductive films by casting the solution onto a substrate and allowing it to dry. However, the resulting films may exhibit blistering, i.e. loss of adhesion, upon exposure to moisture or high humidity. In addition, they suffer from resistance fluctuations that occur as a result of moisture fluctuations, as HA can expand and contract, changing the junction resistance between CNT-CNT contacts. To protect the CNT/glycosaminoglycan resistive heating layer from moisture, it is desirable to cover the layer with a protective film.

A preferred CNT dispersion can be formed by combining a glycosaminoglycan such as hyaluronic acid sodium salt (HA) and carbon nanotubes (CNTs) in water. Preferably, a mass ratio in a range from about 1:1 to about 1:2 of CNTs to HA are combined in water. The loading of CNTs can be between 0.1 and 0.3 weight % to obtain a solution viscosity at 30/s in the range of 50 to 200 cP. In forming the CNT dispersion, the glycosaminoglycan may be first dissolved in a volume of water. The CNTs may then be added to the HA (or other glycosaminoglycan) solution, and additional water added to bring the suspension to a desired total volume. The suspension of CNTs in the HA solution may be sonicated to make a homogeneous dispersion of the CNTs. The CNT dispersion is applied onto a surface to form a CNT network layer over the surface. The resulting highly porous CNT layer comprises glycosaminoglycan(s) and CNTs, preferably in a mass ratio of between 3:1 to 1:3, more preferably 2:1 to 1:2, and still more preferably 1.3:1 to 1:1. Preferably, the CNT layer is then treated with an aqueous acid rinse (pH=2.5), preferably using aqueous citric or phosphoric acid. The resulting (optionally, rinsed) film may then treated with a primer and/or a barrier layer. One preferred barrier layer is Diofan® B204, which is a polyvinylidine chloride (PVDC) copolymer. Compositions such as an epoxy primer or blocked isocyantes (such as Trixene Aqua BI 220) may also serve to form the primer layer. Finally, a polymer topcoat, preferably polyurethane, is applied over the surface.

Typically, the dispersion comprises primarily water, glycosaminoglycan(s), and CNTs. In some embodiments, the dispersion comprises at least 90 mass %, or at least 95 mass % water, glycosaminoglycan(s), and carbon associated with the CNTs (i.e., CNTs and carbon impurities that may coexist with the CNTs). In some other embodiments, the dispersion may further comprise an adhesive composition (such as an acrylate) that increases adhesion of the CNTs to the foam substrate; when present, the adhesive composition preferably comprises 0.5 to 40 mass %, or 1 to 10 mass % of the dispersion. The resistive heating layer may comprise adhesive, for example, 1 to 40 or 1 to 20 or 1 to 10 mass % of the resistive heating layer may comprise one or more adhesives.

The flexible resistive heaters that are described here preferably utilize conductive CNT or graphene particles to conduct an electric current. These particles provide superior results as compared to metal foils because the particles can reversibly slide during deformation without rupturing or crinkling. Dispersions of graphene can be made as described above for CNTs or, alternatively, by other conventional methods.

For any of the descriptions in this specification, the CNT can, in alternative embodiments, be partly or fully replaced by graphene. Due to the similarity in properties between CNTs and graphene, it is believed that the substitution of graphene for CNTs would be successful. Other substitute materials could be identified through routine experimentation in view of the descriptions herein.

The use of carbon-based conductors is additionally advantageous because the resulting pads are radiolucent and a patient can be x-rayed while remaining on a pad.

The CNT coatings can be formed on the foam by solution coating processes such as spray application, screen printing, dip coating, curtain coating, gravure printing, inkjet printing, or other wet casting processes. The preferred conductive coatings are those with high bulk conductivity after drying, greater than 10 S/cm, more preferably greater than 100 S/cm. This allows the use of very thin films, less than 50 μm or more preferably less than 5 μm, as heating elements in a relatively thick foam. Surprisingly, these thin films have excellent adhesion to the foam, even during repeated stretching during compression. They do not impact the mechanical properties of the foam, so the foam still serves as a good pressure management system. Another surprising advantage of the CNT coated foams is their exceptionally high thermal uniformity (i.e., lack of hot spots) during compression and even during unequally applied compression such as when a person lies on a pad or head rest.

Another surprising result is the penetration of the highly polar CNT dispersion into the body of the hydrophobic polymeric foam. The resistance can be decreased by infusing more deeply into the foam, while still retaining only a thin layer on the cell walls. In preferred embodiments, the CNTs infuse at least 1 mm or at least 2 mm into the foam. In some preferred embodiments, the foam has a thickness of at least 1 cm, preferably at least 5 cm, and at least 90 mass % of the CNTs are in the outermost 10% or outermost 5 mm, or outermost 2 mm of the foam in the direction of thickness (not including any protective overlayer(s). The dimensions of the foam in the final article are dictated by the use of the foam; for example, where the foam is a torso pad, it will have dimensions appropriate for that use. Sheets or rolls of the material can be produced in an industrial process and cut to an appropriate size. The pre-cut sheets could have width dimensions in the range of 0.5 to 5 m, length of any size, for example at least 1 m or at least 10 m, or in the range of 0.5 to 100 m; and thickness of at least 1 cm, or least 5 cm, in some embodiments in the range of 1 to 20 cm, or 1 to 10 cm.

Figure 2:
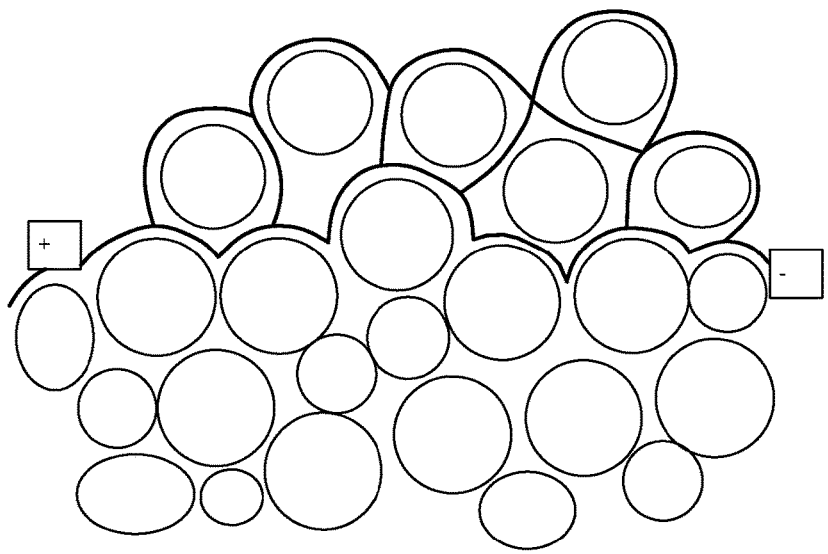
FIG. 2 is a schematic illustration of foam cells coated with a conductive layer that contacts electrodes.

The following discussion and figure presents a theoretical description of the foam's structure. This discussion is not intended to limit the invention to these theoretical structures. The circles in FIG. 2 illustrate the walls of the open cell foam. The thicker line represents the conductive coating attached to the positive and negative leads (squares in the figure) providing the current flow. The conductive material can infuse into the foam and can coat the cell walls.

Bus bars may be applied on top of the foam or on the edges of the foam. Suitable materials for making bus bars are silver-based adhesives or inks, adhesive-backed Cu tape, or other flexible/elastomeric materials. A dielectric layer is applied as a protective coating over the top of the conductor. Suitable coatings include low durometer silicones, polyurethanes, nylons and other polymeric (polyimide, polyethylene terephthalate) as coatings or similar materials as fabrics. An example of a suitable silicone is Ecoflex 00-20, an elastomeric silicone with dielectric strength $1.4 \times 10^7$ V/mm, which preferably uses a 3.5 μm thick layer if powered at 36 V.

A resistive heater is made by connecting an electrical conductor between two electrical leads, or bus bars, and passing current through the resistive heating layer (preferably a CNT layer). The passage of current through a conductor generates heat that scales with the current (I) squared. Under most practical applications, the device is controlled by fixed voltage (V) inputs and the power generated from the heater scales as $V^2/R$, where R is the resistance between the leads. The actual temperature measured at the surface depends on various heat transfer and heat loss mechanisms.

To provide resistive heating, a current is applied through electrical leads (also called busbars) that are connected to the CNT layer at one end and to a power source at another end. The electrical leads may be any electrically conductive material; however, conductive braids and especially copper braids are preferred. The leads may be sewn onto the surface of the flexible foam which conforms around the leads. This intimate contact ensures low contact resistance and efficient heating throughout the entire device. Surprisingly, it was discovered that a nonconductive thread can provide a low resistance electrical connection between the electrical leads and resistive heater on a flexible device, especially where the resistive heater is a flexible CNT layer disposed on the surface of a foam (especially where the resistive layer penetrates into the foam, for example, penetrates in the range of 0.2 mm to 3 mm into the foam). Nonconductive materials can be natural materials (such as cotton) or polymeric materials such as a nylon, polyurethane, polyamide, or polyester.

Figure 3A:
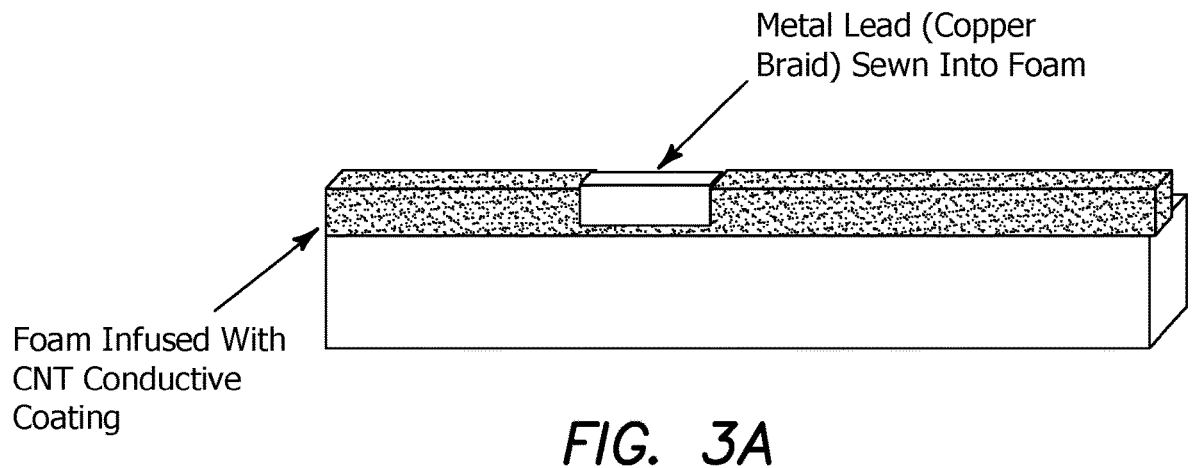
FIG. 3A illustrates an electric lead sewn into a conductive foam.
Figure 3B:
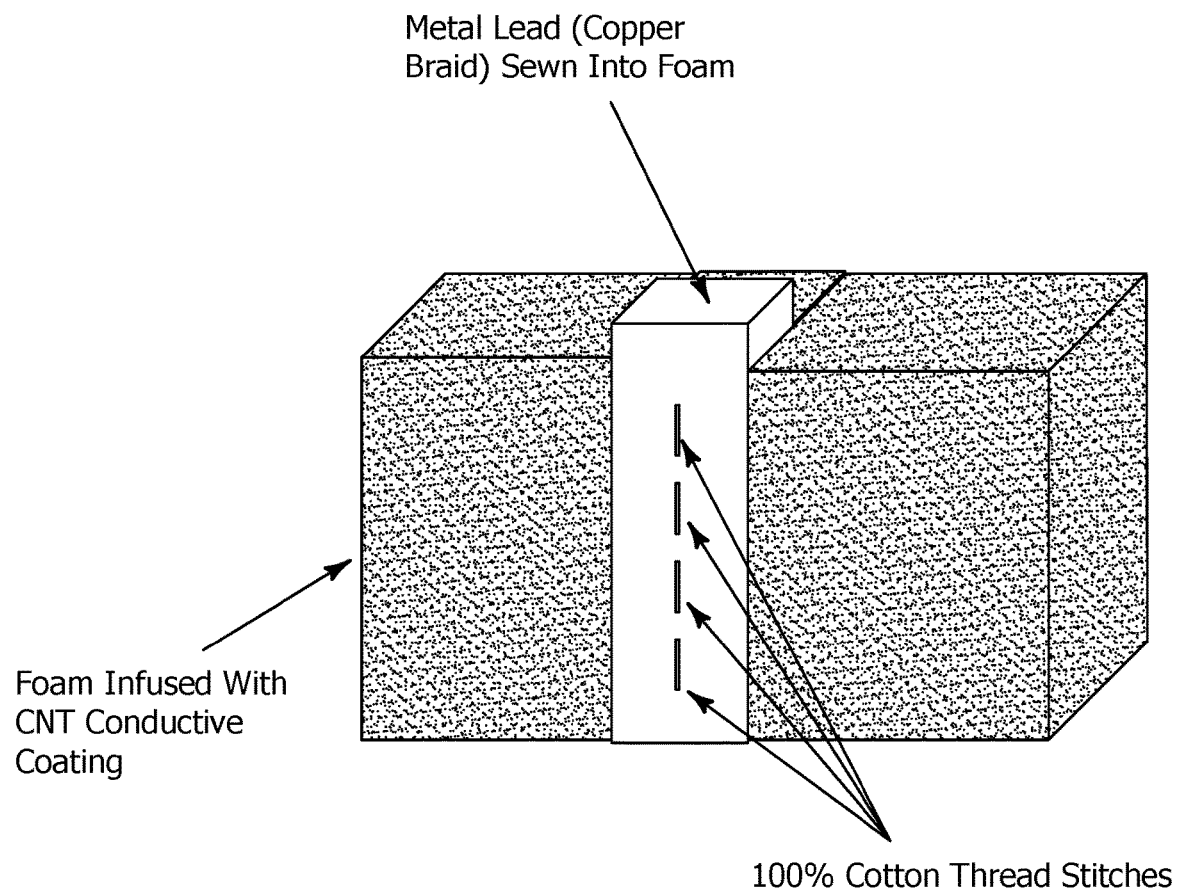
FIG. 3B illustrates the stitches that pass through an electrode.
Figure 3C:
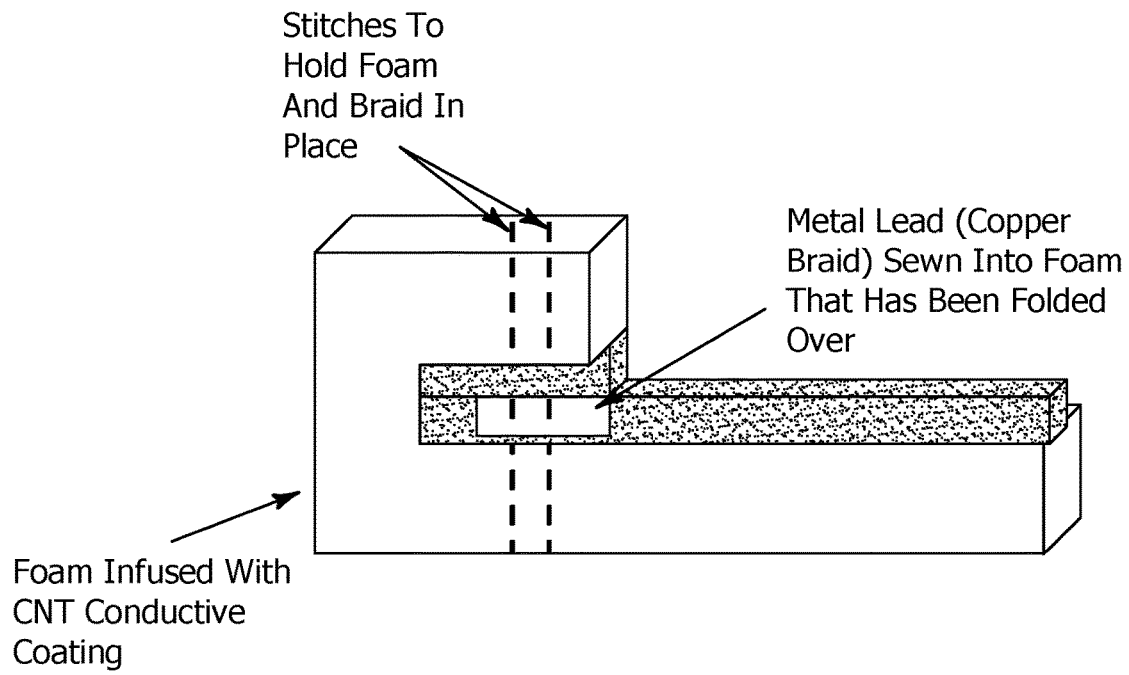
FIG. 3C illustrates a configuration in which a foam is folded over an electrode and stitched into place.

Electrical leads sown into a foam infused with a conductive coating is shown in FIGS. 3A-3C. FIG. 3C illustrates a configuration in which a foam is folded over an electrode to provide intimate contact of the conductive layer with all sides around the circumference of the electrical lead.

The stitches used to hold the electrical leads to the foam are preferably made using a nonconductive thread, and can be applied using a sewing machine. Application of a conductive coating onto a foam surface can create a resistive heater. The conductive coating may be formulated with a suitable binder to ensure adequate adhesion of the coating to the foam for desired lifetime and application use. The busbars are applied either before or after the coating is applied, and located to ensure minimal effect on flexibility. An appropriate dielectric layer, such as a urethane elastomer film, is applied over conductive coating to maintain desired flexibility and to improve durability. A separate power source and controller can be selected to deliver and maintain a desired temperature.

By applying the CNT layer to a foam before the leads are applied, the coating process is simplified and the foam can be coated on a continuous roll via slot die or automatic spray process. The low viscosity CNT coating slightly infuses into the foam and coats the walls of the foam cells yet still has sufficient flexibility and adhesion when dry.

The CNT coating on the foam can be covered with an elastomeric dielectric film such as 0.001" thick polyurethane film to maintain flexibility while providing protection from electrical current. The elastomeric dielectric film is preferably at least 10 μm thick, preferably at least 20 μm thick, and in some embodiments is in the range of 10 μm to 3 mm, more preferably 10 μm to 2 mm thick.

Articles formed using the flexible resistive heater of the present invention include: headrest (pillow); blanket, mattress, OR (operating room) table, guerney cover, seat warmer (such as a car seat warmer), heatable clothing, diving undergarment, and wound healing cover.

Fabric Systems with Conductive Coating

The advantages of the conductive coating can also be used to create fabric-based heaters, such as a scarf, which may be wrapped around the patient's head and/or neck. Fabrics can be, for example, non-woven fabrics comprised of nylon, polypropylene or other material.

Heat Spreading Layer

Heat spreaders can be used to further improve the thermal uniformity. For systems where the heater is under the foam, the addition of a heat spreading layer under or within the memory foam layer(s) (or coated fabric) can dissipate the hot spot caused when the system is nonuniformly compressed. Suitable heat spreading layers are perforated or slitted graphite or thin Al foils, thermal-filled polymers like Parker Therma-A-Gap HCS 1 O or 579, or metallized plastic. Electrically conductive heat spreaders need to be electrically isolated from the heater or there will be shorting, dielectric failure. Coated foil can be electrically insulated if a coating with the proper dielectric strength is used, such as polyethylene terephthalate, nylon or other suitable materials. Encapsulated phase change materials (PCM) such as from Microtek can be added to the dielectric coating placed on top of the CNT coatings. These materials preferably have heats of fusion that exceed 200 J/g and a melting point near 39° C., for example in the range of 35 to 41° C. Assuming hot spots draw 5 W/m² more heat flux than non-hot spots, a layer as thin as 0.6 mm comprising the PCM can thermally eliminate hot spots for times up to, or exceeding, 6 hours.

Delivery of Volatile Compositions—The resistive foam heaters described here can be further infused with a composition which, when heated, generates a gas or aerosol. The foam is preferably an open cell foam or a foam containing voids, or modified with channels. In some embodiments, a foam can be infused with multiple compositions; for example, compositions in separate sections (distributed by length, width, and/or thickness) of the foam. Volatilization (either with or without reaction) of the various compositions can be controlled by applying heat in selected sections; thus, the multiple compositions can be volatilized simultaneously, sequentially, or individually addressable. The CNT layer can be coated with a dielectric layer or layers that have a surface that adsorbs a desired compound. Alternatively, or in addition, the CNT-coated foam can be infused with a composition and then covered with a perforated or permeable coating. The composition to be adsorbed onto the surface or infused into the CNT-coated foam can be, for example, a fragrance, drug, prodrug, or insecticide. In the case of a fragrance, the electrical leads to the foam can be connected to electrical prongs that can be plugged into a wall socket. In another embodiment, the gas or aerosol may comprise a chemoattractant, such as octenol, that attracts a pest to the foam where it is then killed, for example by heat or electricity.

EXAMPLES

Example 1

A conductive dispersion was prepared by dispersing unpurified OCSiAl single wall carbon nanotubes (SWNTs) in a solution of sodium hyaluronate using ultrasonication. The resulting dispersion had a sheet resistance of 1.5 Ω/square when cast as a droplet on glass. This dispersion was diluted with water and spray applied to a viscoelastic foam. Bus bars were applied by attaching copper braided leads to the foam surface with conductive silver epoxy.

Example 2

The dispersion from Example 1 was used to infuse an entire foam substrate. The foam was immersed in the dispersion, removed and air dried. The coating completely coated the cell walls, forming an interconnecting conductive pathway through the foam. Silver epoxy bus bars were added along two opposing edges on one of the square faces. Leads were soldered to conductive copper tape, which were in turn adhered to the silver bus bars. To improve conductivity between the copper tape and bus bars, a push pin was used to create several small punctures in the tape, pushing it down into the silver epoxy and foam. The resistance at the leads, uncompressed, indicate the sheet resistance was approximately 25 Ω/square. The sample generated the target heat at 5 V.

Example 3

A foam substrate was prepared be applying busbars of copper braided leads attached to the foam surface with conductive silver epoxy. CNT dispersion (OCSiAl water based Tubali Coat) was spray applied to top surface of memory foam. Two samples were prepared and tested for thermal and pressure performance. 8"×8" samples and a 20"×20" sample. For thermal testing, a free-standing, pre-cured silicone film silicone dielectric film was placed over top of the sample. Thermal imaging with an IR camera showed that the thermal uniformity is excellent. Measurement of the temperature at the surface using thermocouples separated by several inches showed that the temperature uniformity is ±0.4° C. Thermal imaging indicated a temperature range over the entire sheet (excluding the edges) was highly uniform in the range of about 30 to 31° C. The difference between temperature in an uncompressed and compressed state was determined by testing in an adiabatic box, where the CNT heater was used to warm the sample. The temperature difference between the steady state value with heater at 39° C. and 15 minutes after putting 86.5 mmHg pressure on an area was less than 2° C. In contrast, the temperature difference for systems where the heater was placed underneath the foam was greater than 3° C.

Differences in pressure management were measured for a heater as prepared in Example 3, either with a free-standing silicone dielectric or a case where the heater was coated with the silicone dielectric.

Example 4 (Contemplated Example)

Another embodiment of this heater may be with the addition of a binder resin to the conductive coating to achieve desired adhesion to the polyurethane foam. A water based conductive coating would be compatible with various waterbased polymer emulsions such as polyurethanes and acrylics for adhesion improvement.

Example 5

The CNT dispersion was applied to the inside of a Nylon fabric, which had a hydrophobic surface treatment. The coating was attached to copper foil bus bars. In this embodiment, the patient would be in contact with the hydrophobic outer portion. The coated fabric maintains good flexibility during handling.

Attaching Leads—Comparative Example—Eeonyx Fabric Heater (Similar to U.S. Pat. No. 7,786,408)

Figure 4:
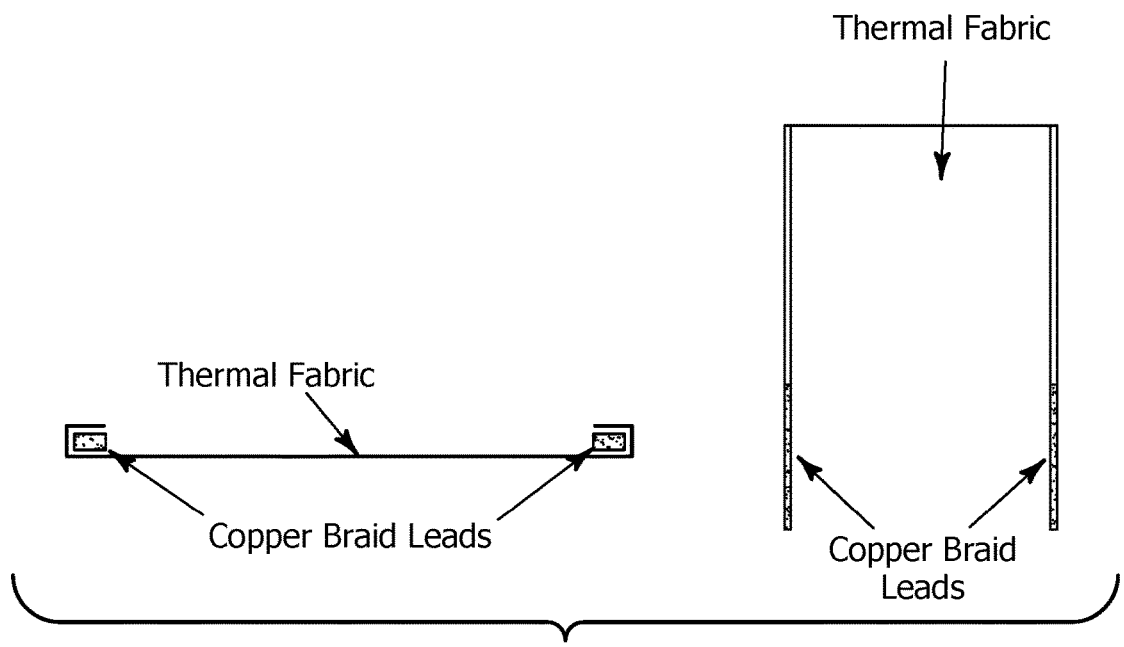
FIG. 4 is an overhead (right) and side (left) view of a thermal fabric wrapped around electrical leads to form a heater.

A 6.5"×6.5" size of Eeonyx thermal warming fabric was prepared into a resistive heater by sewing HexWik W55 copper braids onto two sides. The fabric was creased to create a ¼" fold, the copper braid was placed into the fold and a single line of cotton thread stitching held the lead in place. See FIG. 4.

Example—Coated Foam with Sewn Leads Plus Coating over Leads

A 20"×40"×0.25" piece of polyurethane viscoelastic memory foam was coated with an aqueous CNT dispersion and polyurethane binder formulation (47.6 wt % Tuball Coat E+47.6 wt % deionized water+4.8 wt % Helmsman Urethane) then allowed to air dry for 16 hours. This was cut into a 6.5"×6.5" piece and copper braid (HexWik W55) was sewn onto two sides with 100% cotton thread (Gutermann CA 02776) to create a 6"×6" heater area. An additional coat of CNT/polyurethane was applied again over the sewn copper leads for added electrical contact.

Example—Coated Foam with Sewn Leads

A 20"×40"×0.25" piece of polyurethane memory foam was coated with an aqueous CNT dispersion and polyurethane binder formulation (47.6 wt % Tuball Coat E+47.6 wt % deionized water+4.8 wt % Helmsman Urethane) then allowed to air dry four 16 hours. This was cut into a 5.5"×5.5" piece and copper braid (HexWik W55) was sewn onto two sides with 100% cotton thread to create a 5"×5" heater area. No additional CNT/polyurethane was applied over this example.

Tests

Figure 5:
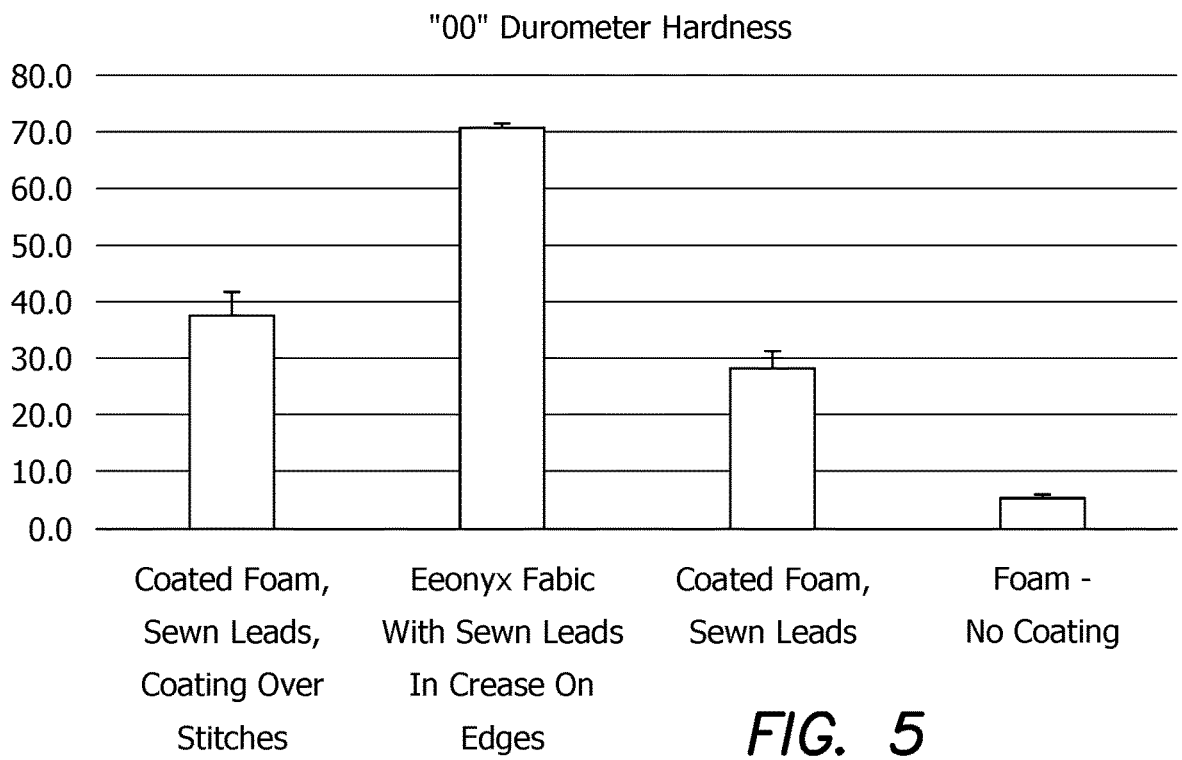
FIG. 5 shows the results of hardness measurements for 4 different materials.

The "00" durometer hardness of each coated foam samples and an uncoated foam sample was tested per ASTM D2240 using a Rex® Model DD-4 digital Durometer mounted on a OS-1 stand. Averages and standard deviation calculated from durometer readings taken in 5 unique areas of the heater. This equipment provides a maximum durometer reading to a 0.1 resolution. All tests were performed on a ¼" thick foam. The Eeonyx heater was placed on top of the foam for a comparison of the hardness. The graph below shows the results. While the conductive coating increases the hardness of the foam slightly, the Eeonyx fabric is significantly harder and less flexible than the coated and uncoated foams. See FIG. 5.

Figure 6:
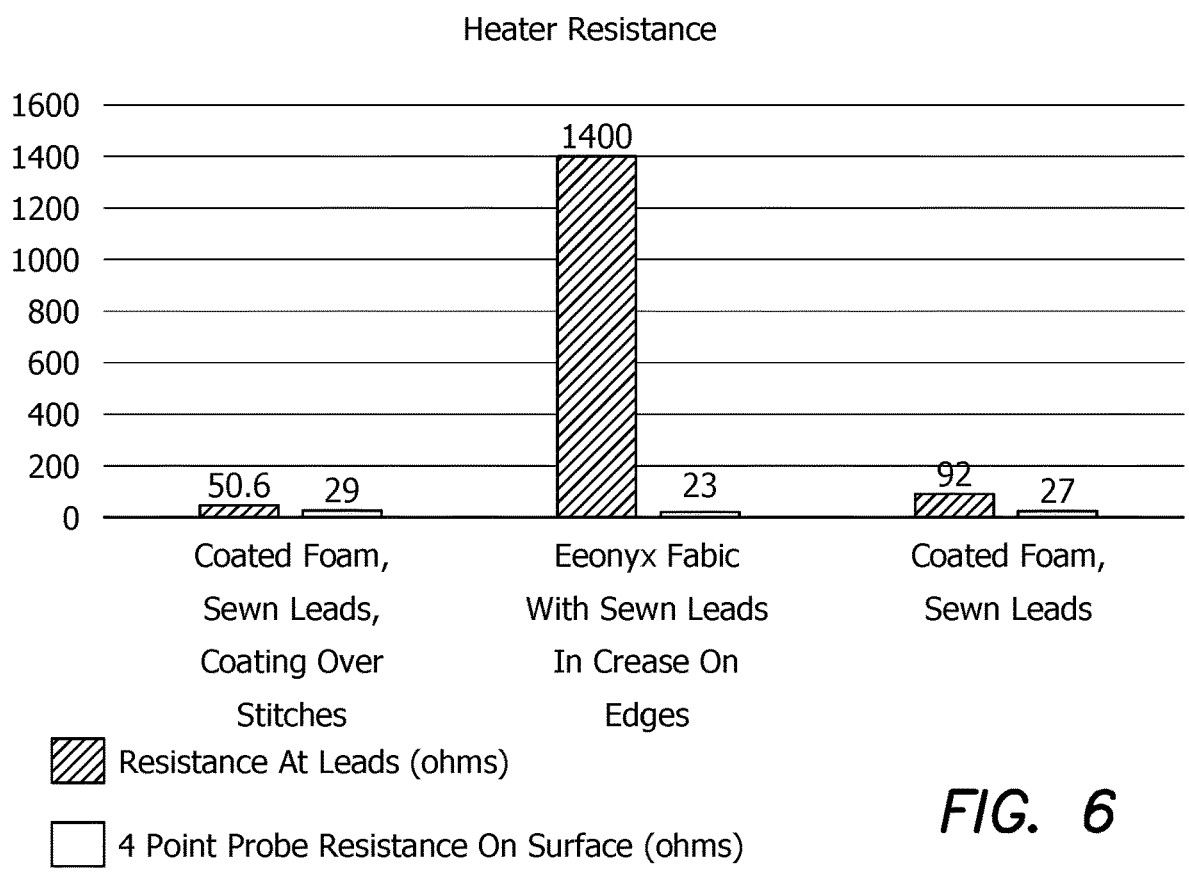
FIG. 6 shows the resistance at the leads (shaded bars) and surface resistance of: a prior art (Eeonyx) heatable fabric, a coated foam with leads sewn into the foams, and a coated foam with sewn threads and a coating over the stitches.

The surface resistance of the heaters was measured using a 4 point probe. This result can be compared to the resistance measured at the copper leads using a Fluke ohm meter. When the copper leads have poor electrical contact to the heater surface, the heating efficiency will be poor. Contact resistance is estimated to be the increase in resistance between the surface measurement and the lead measurement. Ideally, the surface resistance and lead resistance measurements will have little difference and the contact resistance will be very low. The samples were tested for both surface resistance and lead resistance. The results are in the graph shown in FIG. 6.

Figure 7:
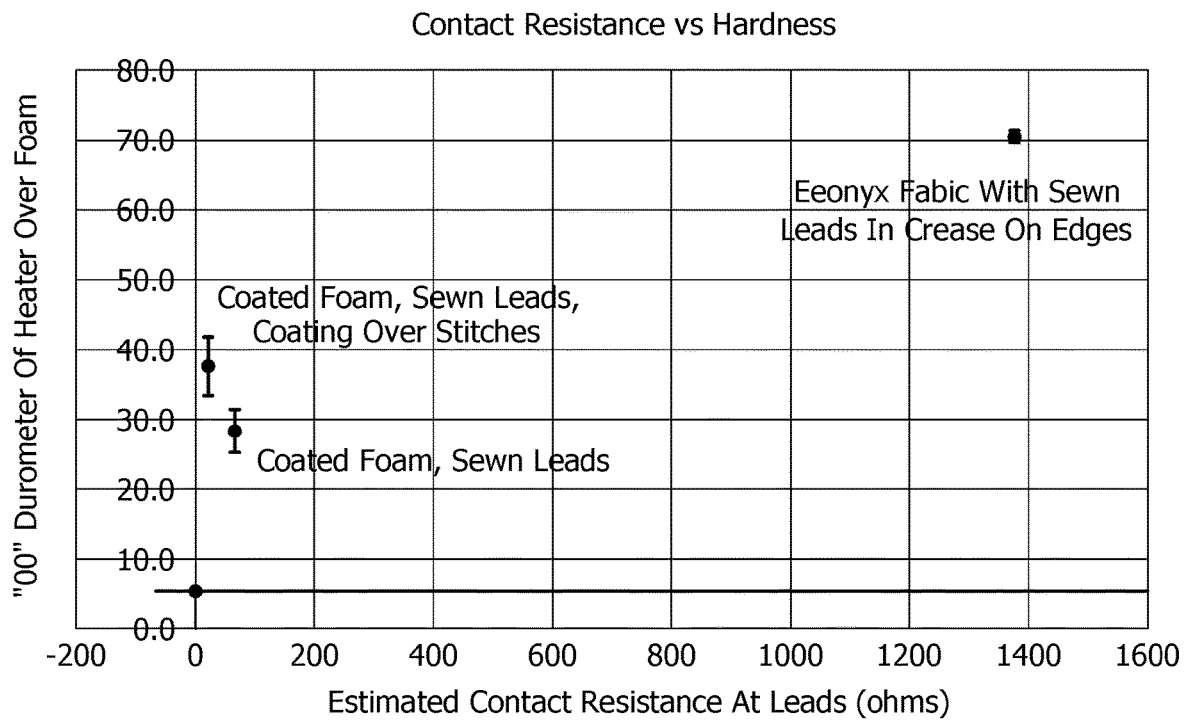
FIG. 7 shows hardness as a function of estimated contact resistance for three different resistive heaters.

The difference in the resistance at the leads and the 4 point probe surface resistance of the Eeonyx heater is substantial and the result is a very high contact resistance for this type of heater. The fabric does not have good electrical contact with the copper leads because it is not as flexible as the foam and does not conform to the braid surface. The ideal flexible heater has very low contact resistance and very low hardness (better flexibility). The graph below shows the contact resistance vs the hardness results for the three heaters. The lowest contact resistance occurs when additional conductive coating is applied over the leads and provides additional electrical contact to the heater surface. The leads stitched on the heater foam without additional coating have slightly higher contact resistance but since the foam conforms around the copper braid, the contact resistance is still much lower than with the stiffer Eeonyx fabric heater. See FIG. 7.

Figure 8:
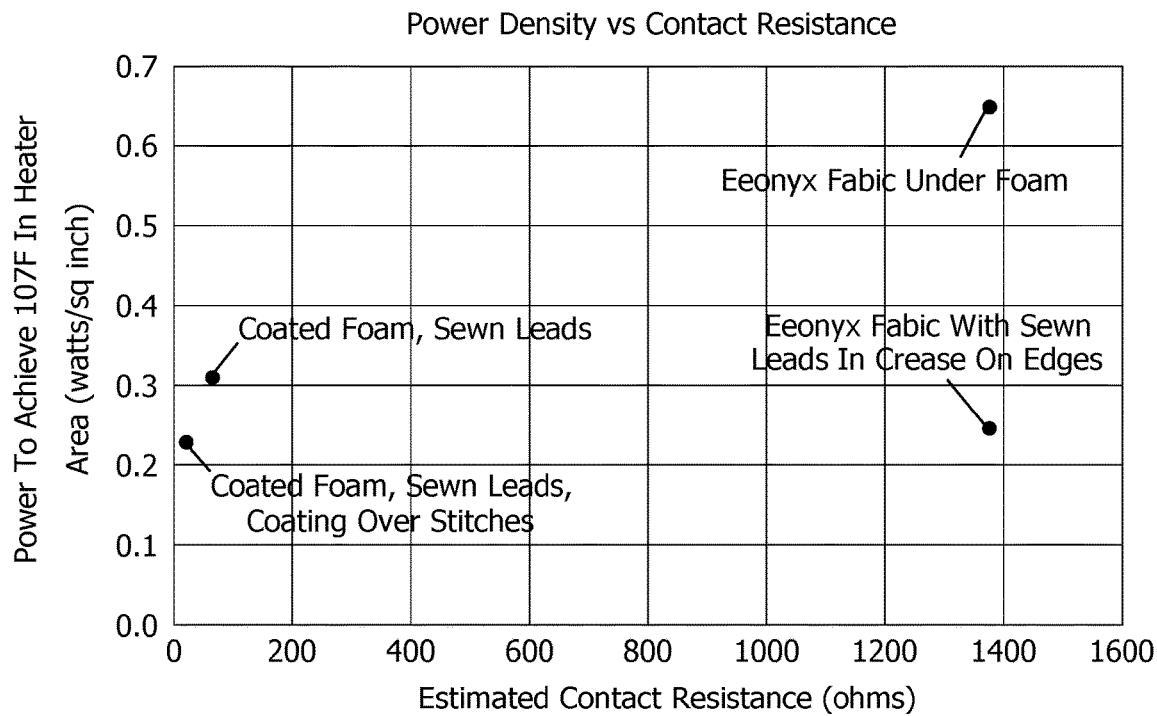
FIG. 8 shows the estimated contact resistance that correlates with power to achieve a surface temperature of 107° F. (41.7° C.). For the embodiments in which the resistive layer is on the surface, the surface layer temperature and surface temperature are the same.

The power required per unit area to heat to the desired temperature is the power density of the heater. A lower power density is more efficient and more desirable. A high contact resistance requires more voltage to reach the desired temperature of the entire heater assembly. This is not only a waste of energy, but also can heat up the leads to an unsafe temperature. The graph in FIG. 8 shows the power density vs the contact resistance of each heater system. The heating system with the lowest power density (best power utilization) is the coated foam with additional coating over the stitched leads.

Figure 9:
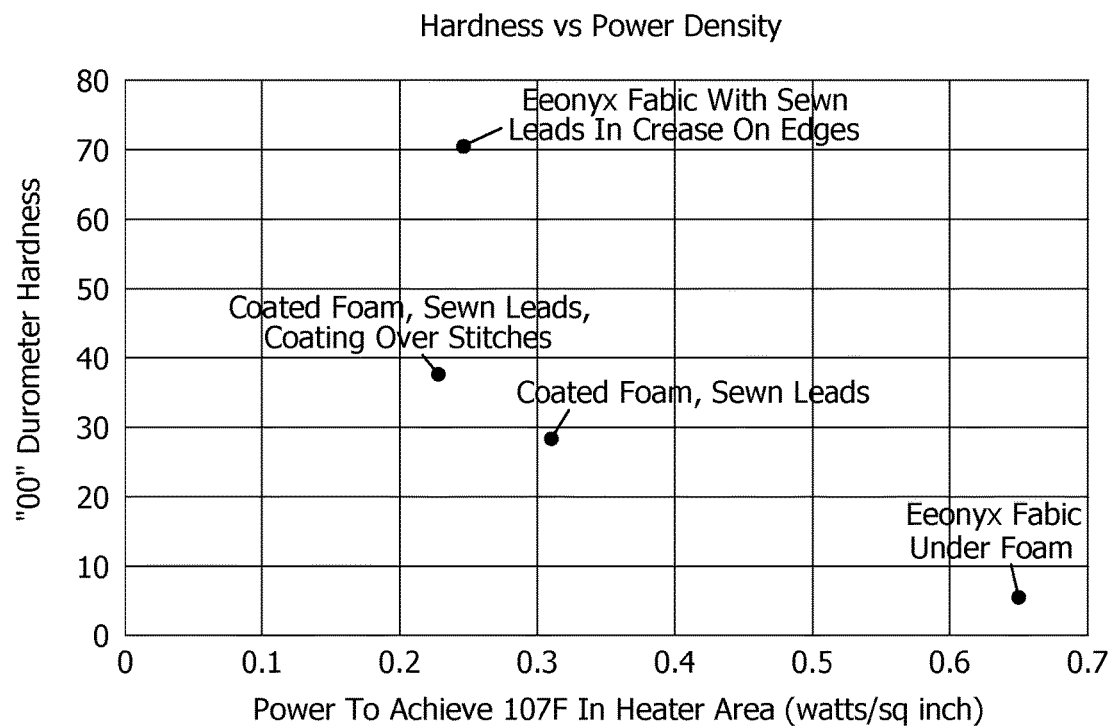
FIG. 9 shows hardness as a function of the power needed to achieve a surface temperature of 107° F. (41.7° C.) for four resistive heaters.

The Eeonyx fabric heater was tested under a ¼" thick piece of foam to provide more flexibility at the top surface. This strategy is described in the prior art to permit better pressure management for patient warming pads. Since the foam acts as thermal insulation, more power is required to reach the desired temperature. The graph below shows the hardness versus power density. While the Eeonyx fabric heater under the foam has the lowest hardness, it also requires the most power and is inefficient at power utilization. The coated foam samples provide both the low hardness (more flexible heater) and low power density for best heating efficiency. See FIG. 9.

Figure 10:
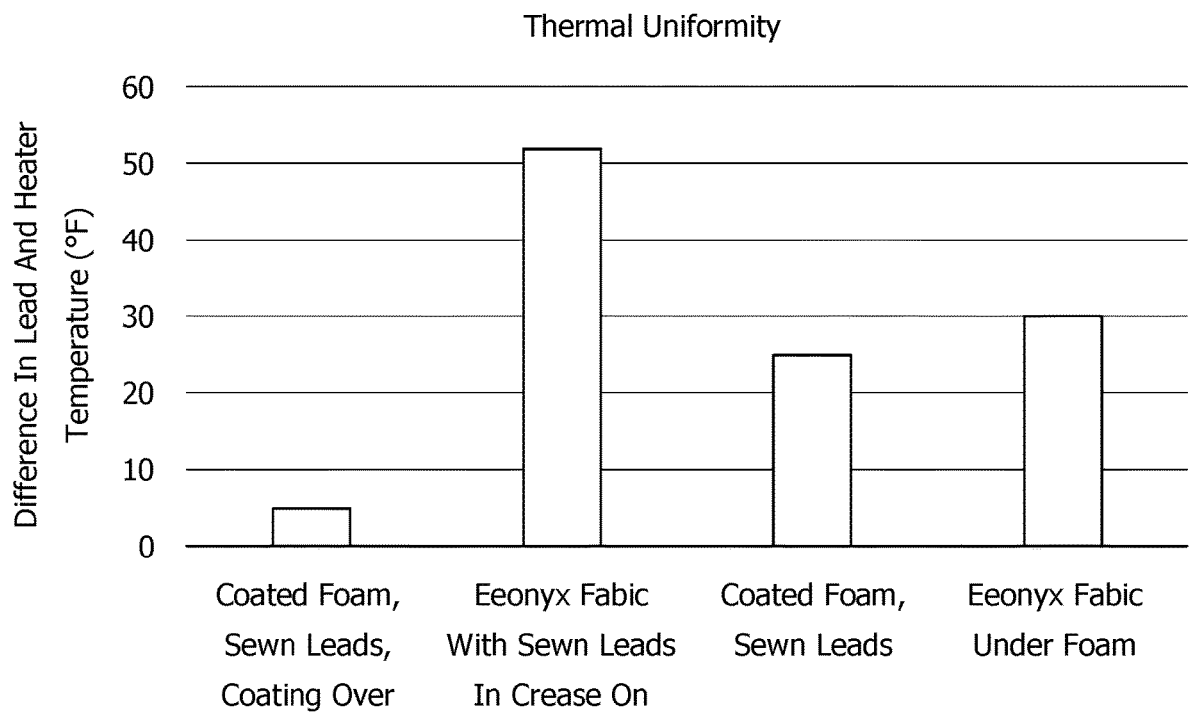
FIG. 10 shows the temperature difference between the lead and the heater for four resistive heaters.

Further illustrating the improvement in effective contact resistance, the temperature of the center of the heater is compared to the temperature at the copper lead using thermal imaging. Poor electric contact between the copper braid lead and the heater will increase the contact resistance and cause more current to flow into the lead increasing temperature. The graph in FIG. 10 shows the thermal uniformity of the heater examples. The best uniformity is seen with the coated foam with additional coating over the stitched leads with only 5° F. (3° C.) difference in temperature between the leads and the center of the heater area. The Eeonyx fabric heater has a difference of 52° F. (30° C.) between the leads and the center of the heater due to the poor electric connection and high contact resistance.

The graphene or graphene oxide could be used in the same technique as the carbon nanotubes if they are applied as a liquid dispersion.

Any of the resistive heaters of the invention, may, in some preferred embodiments, be further characterized as possessing one or any combination of the properties illustrated in the Examples. For example, a durometer hardness (measured according to ASTM D2240) of 10 to 50 or 20 to 40; leads attached to the foams having a contact resistance of 50 to 600 ohms, or 50 to 400 or less than 200 ohms; a 4 point probe on the surface having an average resistance of 10 to 200 ohms, or 20 to 100 ohms (or ohms per square); or a power density of 0.1 to 0.5 W/in$^2$ about 0.2 to 0.5 W/in$^2$; or about 0.2 to 0.4 W/in$^2$ or about 0.2 to about 0.3 W/in$^2$ necessary to increase temperature from room temperature (about 75° F. (24 C)) to 107° F. (41.7° C.); and/or a temperature difference for a heater in which the electrical leads are separated by at least three inches or at least 5 inches having a maximum variation of temperature between the leads and the surface of the heated area of 30° F. (16.7° C.) or less, preferably 25° F. (13.9° C.) or less, more preferably 20° F. (11.1° C.) or less, still more preferably 10° F. (5.5° C.) or less, and in some embodiments in the range of 3 to 10° F. (1.7 to 5.5° C.) or less.

What is claimed:

1. A resistively-heatable flexible, foam, comprising:
   a flexible, polymeric solid foam;
   a resistively-heatable CNT, graphene, or graphene oxide layer disposed on the exterior and at least partly within the foam;
   wherein the resistively-heatable layer is characterizable by an average resistance of 10 to 200 ohms/square as measurable on the surface of the resistively-heatable layer with a 4 point probe; and a polymeric film disposed over the CNT, graphene, or graphene oxide layer.

2. The resistively-heatable flexible, foam of claim 1, further comprising a composition disposed within the foam and in thermal contact with the resistively-heatable CNT layer; wherein the composition is a composition which, when heated, generates a gas or aerosol.

3. The resistively-heatable flexible, foam of claim 2, wherein the heat releasable composition comprises a chemoattractant.

4. The resistively-heatable flexible, foam of claim 3, wherein the heat releasable composition comprises octenol.

5. The resistively-heatable flexible, foam of claim 1, further comprising a heat releasable composition adsorbed on the polymeric film; wherein the heat releasable composition is a composition which, when heated, generates a gas or aerosol.

6. A fragrance-releasing wall plug comprising the foam of claim 2 wherein the heat releasable composition comprises a fragrance; wherein the heat releasable composition is a composition which, when heated, generates a gas or aerosol.

7. An inhaler, comprising the foam of claim 2 wherein the heat releasable composition comprises a drug or prodrug; wherein the heat releasable composition is a composition which, when heated, generates a gas or aerosol.

8. The resistively-heatable flexible, foam of claim 1, wherein the resistively-heatable CNT, graphene, or graphene oxide layer comprises at least 2 mm into the foam.

9. The resistively-heatable flexible, foam of claim 8, wherein the resistively-heatable CNT, graphene, or graphene oxide layer has a thickness of at least 1 cm wherein at least 90 mass % of the CNTs are in the outermost 5 mm.

10. The resistively-heatable flexible, foam of claim 1, wherein the resistively-heatable CNT, graphene, or graphene oxide layer is in the form of a sheet having a width in the range of 0.5 to 5 m, length of at least 1 m, and thickness of at least 1 cm.

11. The resistively-heatable flexible, foam of claim 1, wherein the resistively-heatable CNT, graphene, or graphene oxide layer is covered with an elastomeric dielectric film having a thickness in the range of 10 μm to 3 mm.

12. An article comprising the resistively-heatable flexible, foam of claim 1, wherein the article is selected from the group consisting of: pillow, blanket, mattress, operating room table, gurney cover, seat warmer, heatable clothing, diving undergarment, and wound healing cover.

13. The article of claim 12 comprising at least two electrical leads attached to the foam and electrically connected to the resistively-heatable layer.

14. A resistively-heatable flexible, foam, comprising:

a flexible, polymeric solid foam;

a resistively-heatable layer disposed on the exterior and at least partly within the foam;

at least two electrical leads attached to the foam and electrically connected to the resistively-heatable layer; and further characterizable by: a surface hardness, measured according to ASTM D2240 on the exterior of the heatable flexible foam that is nearest the heatable layer, of 10 to 50; the leads having a contact resistance of 50 to 600 ohms when current is applied to the electrodes; the exterior having an average surface resistance of 10 to 200 ohms; a power density of 0.1 to 0.5 W/in$^2$ necessary to increase the average temperature of the resistively-heatable layer from 75° F. (24 C.) to 107° F. (41.7° C.); and/or where the electrical leads are separated by at least three inches and having a maximum variation of temperature between the leads of 20° F. (16.7° C.) or less of the resistively-heatable layer when the average temperature of the resistively-heatable layer between the leads is raised to 107° F. (41.7° C.).

15. The resistively-heatable flexible, foam of claim 14 where the exterior of the heatable flexible foam that is nearest the heatable layer, having a surface hardness of 20 to 40.

16. The resistively-heatable flexible, foam of claim 14 wherein the leads have a contact resistance of 50 to 400 ohms when current is applied to the electrodes sufficient to raise the temperature of the layer to 107° F. (41.7° C.).

17. The resistively-heatable flexible, foam of claim 15 wherein the electrical leads are separated by at least five inches and wherein a maximum variation of temperature between the leads and a surface of the heated area is 20° F. (11.1° C.) or less when the average temperature of the layer is raised to 107° F. (41.7° C.).

18. The resistively-heatable flexible, foam of claim 14 characterizable by a power density of 0.2 to 0.4 W/in$^2$ necessary to increase the average temperature of the layer from 75° F. (24 C.) to 107° F. (41.7° C.).

19. The resistively-heatable flexible, foam of claim 14 characterizable by electrical leads that are separated by at least five inches and wherein a maximum variation of temperature between the leads and a surface of the heated area is 20° F. (11.1° C.) or less when the average temperature of the layer is raised to 107° F. (41.7° C.).

* * * * *